United States Patent [19]

Ohtomo et al.

[11] Patent Number: 5,167,659
[45] Date of Patent: Dec. 1, 1992

[54] BLOOD COAGULATING APPARATUS

[75] Inventors: Naoki Ohtomo; Shizuo Ninomiya, both of Mitaka, Japan

[73] Assignee: Aloka Co., Ltd., Tokyo, Japan

[21] Appl. No.: 699,453

[22] Filed: May 13, 1991

[30] Foreign Application Priority Data

May 16, 1990 [JP] Japan .................................. 2-126444

[51] Int. Cl.$^5$ ............................................ A61B 17/39
[52] U.S. Cl. ......................................... 606/40; 606/42; 606/49
[58] Field of Search ......................... 606/40, 42, 45, 49

[56] References Cited

U.S. PATENT DOCUMENTS 4,060,088 11/1977 Morrison, Jr. et al. ............... 606/49
4,936,301 6/1990 Rexroth et al. ..................... 606/49 X

FOREIGN PATENT DOCUMENTS 3642077 6/1988 Fed. Rep. of Germany ........ 606/49

OTHER PUBLICATIONS

Freitas et al. "Controlled Trial . . . Ulcers", Am. J. Gastroenterology, vol. 80, No. 11, 1985, pp. 853-857.
Reidenbach et al., "Eine neue Methode . . . ", Biomed. Techn., 23 (1978), pp. 71-74.

Primary Examiner—Lee S. Cohen
Attorney, Agent, or Firm—Koda and Androlia

[57] ABSTRACT

A blood coagulating apparatus for stopping bleeding by heating the bleeding portion of the living body while producing an electric discharge on the bleeding portion. A patient plate which is capable of maintaining the state of being electrically connected to the living body is placed on the living body. An active electrode including an electrolyte ejector is brought to the vicinity of the bleeding portion. The electrolyte ejector includes an ejector for supplying an electrolyte to an air passage for passing air therethrough at a high speed so as to mix the electrolyte with air and ejecting the atomized electrolyte to the bleeding portion. The electric discharge produced in the vicinity of the bleeding portion by applying a high-frequency voltage between the active electrode and the patient plate is made stable and effective by ejecting the atomized electrolyte toward the bleeding portion. Thus, a uniform coagulation spot is formed and stable hemostatis is enabled.

18 Claims, 7 Drawing Sheets

BLOOD COAGULATING APPARATUS

BACKGROUND OF THE INVENTION

1. Field of the Invention

The present invention relates to a blood coagulating apparatus which is used for stopping bleeding in a surgical operation or the like and, more particularly, to a blood coagulating apparatus for stopping bleeding by heating the bleeding portion while producing an electric discharge on that portion.

2. Description of the Prior Art

Blood coagulating apparatuses for stopping bleeding by irradiating the bleeding portion with a laser beam or by using an electrosurgical apparatus which utilizes a high-frequency power are conventionally known.

In the former case, the system of the structure of the apparatus is complicated and the price of the apparatus is inconveniently high.

In the latter case, an electrosurgical apparatus such as an electric scalpel is provided with a handpiece equipped with an active electrode, and a patient plate which is connected to a living body in contact therewith. In cutting the portion being operated, the active electrode of the handpiece is brought into contact therewith for establishing electrical conduction and concentratedly heating that portion. When the blood is coagulated by such an electrosurgical apparatus, the active electrode of the handpiece is replaced with a spatula or the like so as to stop bleeding by heating in place of cutting the portion.

As a method of coagulating blood by such an electrosurgical apparatus, what is called spray coagulation has recently been used. This is a method of stopping bleeding by heating the bleeding portion by the arc discharge produced by the dielectric breakdown of the air between the living body and the active electrode which is produced by applying a high voltage such as 5 to 8 kV between the living body and the active electrode in a non-contacting state. According to the spray coagulation, since hemostatis is possible in the state in which the active electrode and the living tissue are not in contact with each other, it is possible to stop bleeding without a fear of cohesion between the active electrode and the tissue.

Although the spray coagulation method using an electrosurgical apparatus which utilizes a high-frequency power is advantageous in that hemostatis of the living body is possible in a non-contacting state, the position and the conditions at and under which an arc discharge is produced are influenced by contingency, which makes it difficult to constantly form a uniform coagulation spot, thereby making a stable hemostatic operation impossible.

SUMMARY OF THE INVENTION

Accordingly, it is an object of the present invention to solve the above-described problems in the prior art and to provide a blood coagulating apparatus which is capable of hemostatic operation in the non-contacting state of an active electrode and the living body and which is capable of forming a uniform coagulation spot.

To achieve this aim, the present invention provides a blood coagulating apparatus having an active electrode which is brought to the vicinity of a bleeding portion of the living body, a patient plate which is capable of maintaining the state of being electrically connected to the living body and a high-frequency signal generator portion for generating a high-frequency voltage so as to stop bleeding by heating the bleeding portion by the arc discharge produced between the bleeding portion of the living body and the active electrode which is produced by applying a high-frequency voltage from the high-frequency signal generator portion between the active electrode and the patient plate, the blood coagulating apparatus comprising:

a liquid ejecting means for ejecting an electrolytic solution from the end of the active electrode toward the bleeding portion of the living body; and a liquid supplying means for supplying the electrolytic solution to the liquid ejecting means;

whereby the arc discharge is produced while using the path of ejection leading from the electrolytic solution to the active electrode as a conduction path.

According to the blood coagulating apparatus having the above-described structure, the electrolytic solution is ejected toward the bleeding portion of the living body by the liquid ejecting means. The path of liquid ejection constitutes a conduction path having a comparatively low impedance between electrodes to which a high-frequency voltage is applied. The present invention has been achieved on the basis of this finding, and the path of the ejected liquid between the active electrode and the living body is used as the conduction path when the arc discharge is produced. In other words, the position at which the arc discharge is produced is not limited to one position on the living body side and the discharge is uniformly produced in the path of the ejected electrolytic solution. Consequently, it is possible to ensure uniform heating operation in the range of the ejected liquid column. Therefore, the coagulation spot is uniform in the range in which the electrolytic solution is sprayed, and better hemostatic operation is realized.

The above and other objects, features and advantages of the present invention will become clear from the following description of preferred embodiments thereof, taken in conjunction with the accompanying drawings. description of preferred embodiments thereof, taken in conjunction with the accompanying drawings.

DESCRIPTION OF THE PREFERRED EMBODIMENTS

Preferred embodiments of the present invention will be explained hereinunder with reference to the accompanying drawings.

First Embodiment

Figure 1:
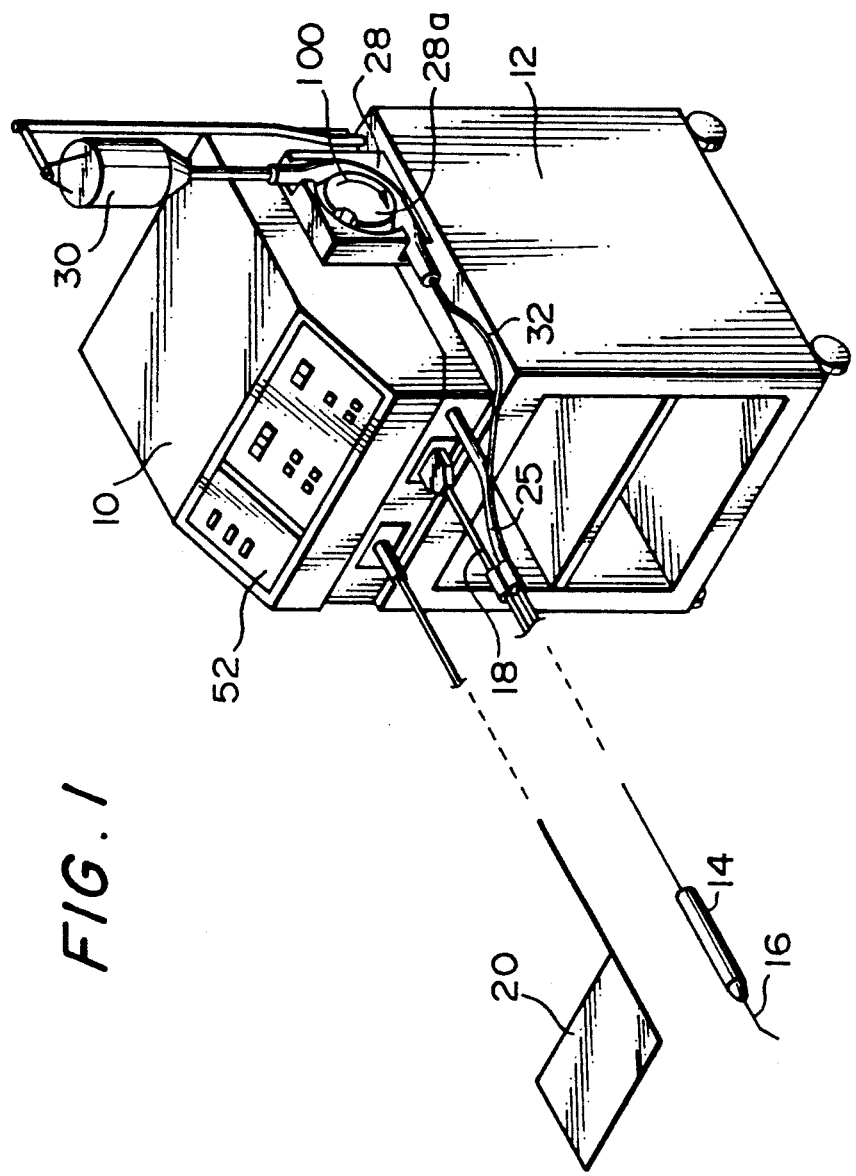
FIG. 1 is a schematic perspective view of the entire structure of a first embodiment of a blood coagulating apparatus according to the present invention.

FIG. 1 is a schematic perspective view of a blood coagulating apparatus according to the present invention. A main body 10 is mounted on a carriage 12 and is movable to any given position with the movement of the carriage 12.

A handpiece 14 is connected to the main body 10 by a cable 18, and an active electrode 16 is attached to the end portion of the handpiece 14. The other electrode, namely, a counter electrode plate 20 is connected to the main body 10, and a high-frequency and high voltage is applied between the electrodes 16, 20 by operating the main body 10.

In FIG. 1, the handpiece 14 and the counter electrode plate 20 are only schematically shown for the purpose of simplifying the drawing.

Figure 2:
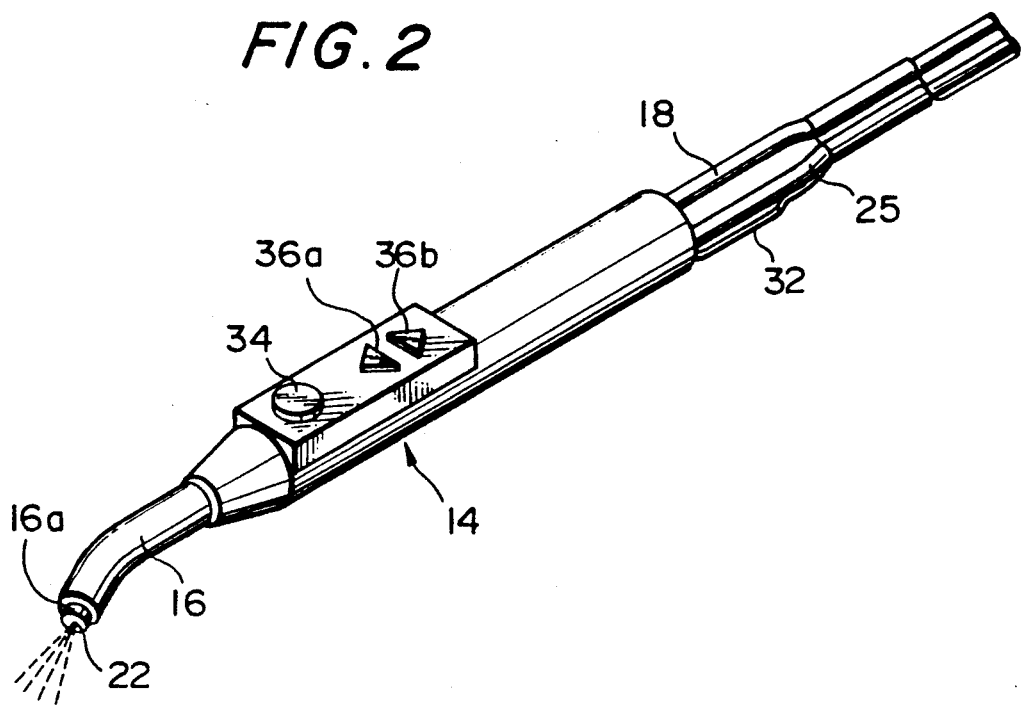
FIG. 2 is a perspective view of a handpiece used in the first embodiment shown in FIG. 1.

FIG. 2 schematically shows the external appearance of the handpiece 14 in the first embodiment. Injection holes 22 for ejecting an electrolytic solution such as physiological saline from the end portion of the active electrode 16 are formed in the active electrode 16 of the handpiece 14 as a component of the liquid ejecting means. The active electrode 16 formed at the end portion of the handpiece 14 is bent at a predetermined angle at the end portion thereof, and the ejection holes 22 are formed at the inner portion of the end portion.

Figure 3:
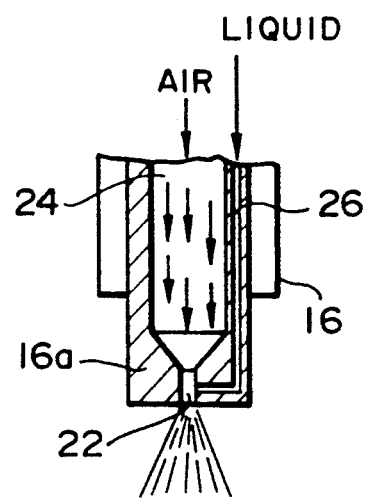
FIG. 3 is a schematic sectional view of the end portion of the handpiece shown in FIG. 2.

FIG. 3 schematically shows the section of the end portion of the active electrode 16. The ejection holes 22 communicate with the hollow portion of the active electrode 16, thereby constituting an air passage 24. A liquid passage 26 as a component of the liquid supplying means is connected to the vicinity of the ejecting portion of the active electrode 16. Compressed air is supplied from an air pump (not shown), which is another component of the liquid ejecting means provided within the main body 10, to the air passage 24 and exhausted from the ejection holes 22 at a high speed. As a result, the liquid is sucked through the liquid passage 26 under a negative pressure, and the electrolytic solution is atomized and ejected to the outside from the ejection holes 22.

In this embodiment, a liquid pump 28 is provided as another component of the liquid supplying means, as shown in FIG. 1. The liquid pump 28 sends out the electrolytic solution stored in a tank 30 toward the side of the handpiece 14 through a liquid tube 32 by the rotation of a roller 28a in the direction indicated by the arrow 100.

The handpiece 14 (see FIG. 2) is provided on the grip portion thereof with a switch 34 for turning on and off the working power and the pump 28, and switches 36a and 36b for increasing or reducing the set value of the working power. The main body 10 and the liquid tube 32 are inserted into the handpiece 14. The wire of the cable 18 is connected to a core portion 16a of the active electrode 16 in which the ejection hole 22 is formed. The core portion 16a is composed of an electric conductive metal such as stainless steel. The air tube 25 and the liquid tube 32 are respectively connected to the air passage 24 and the liquid passage 26 formed within the active electrode 16.

Figure 4:
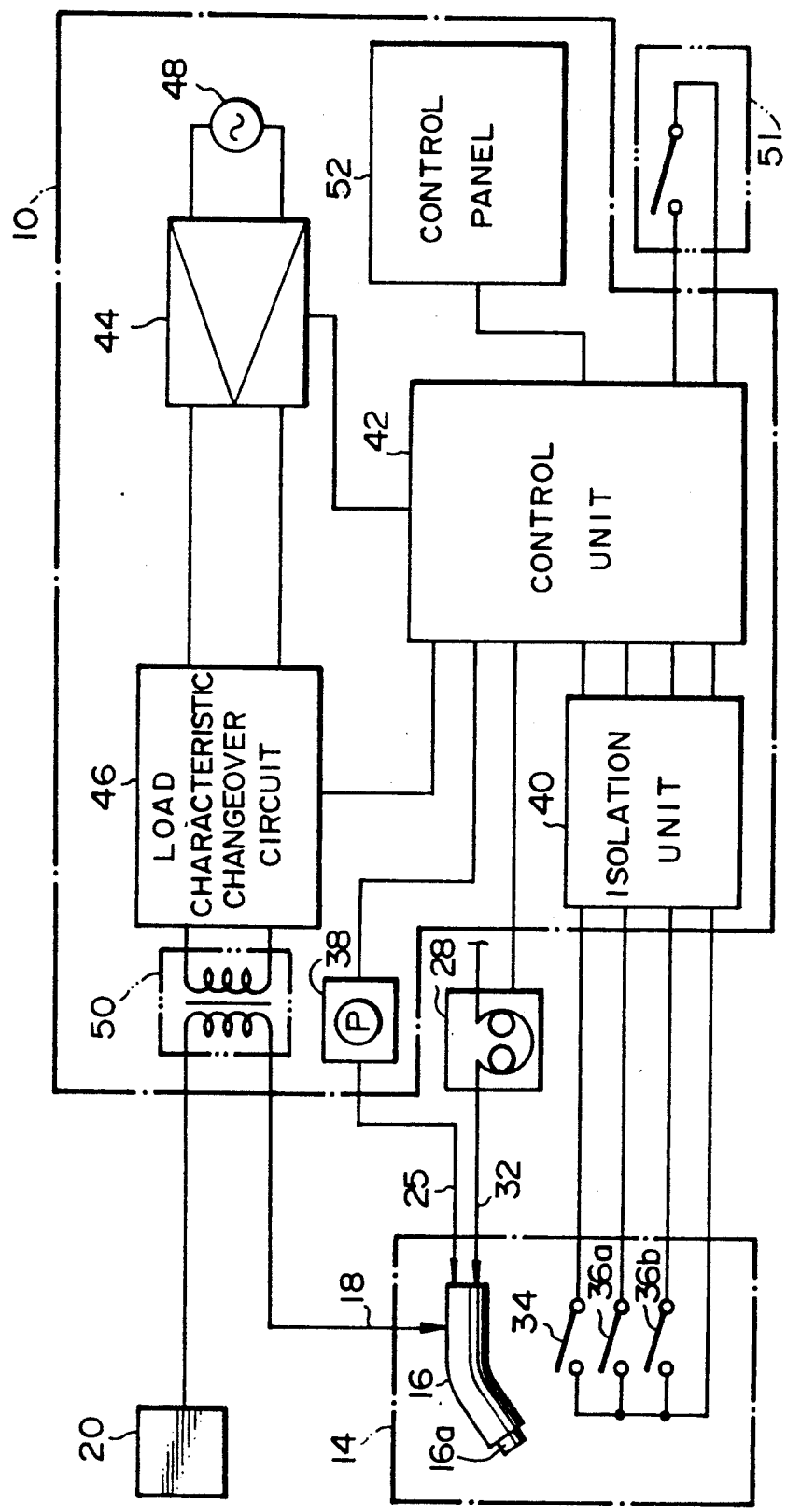
FIG. 4 is a circuit diagram of the first embodiment.

FIG. 4 is a schematic circuit diagram of this embodiment. The operation of this embodiment will be explained with reference to the circuit diagram.

In FIG. 4, each of the switches 34, 36a and 36b provided on the handpiece 14 is connected to a control unit 42 through an isolation unit 40. The isolation unit 40 and the control unit 42 are provided within the main body 10.

To the control unit 42 are further connected an amplifier 44 and a load characteristic changeover circuit 46. The amplifier 44 controls the voltage supplied from a high-frequency signal generator 48 in accordance with a signal of the control unit 42. The load characteristic of the load characteristic changeover circuit 46 is switched between a load characteristic having a peak in a high impedance (1 kΩ to 2 kΩ) and a load characteristic having a peak in a comparatively low impedance (200 to 300 Ω) in accordance with the signal from the control unit 42. A boosting transformer 50 is disposed between the load characteristic switching circuit 46 and the active electrode 16 and the counter electrode plate 20.

A control panel 52 is provided in order to supply a control signal to the control unit 42, and a foot switch 51 is provided so as to switch between ON and OFF of the power by the operation of the foot.

Figure 5:
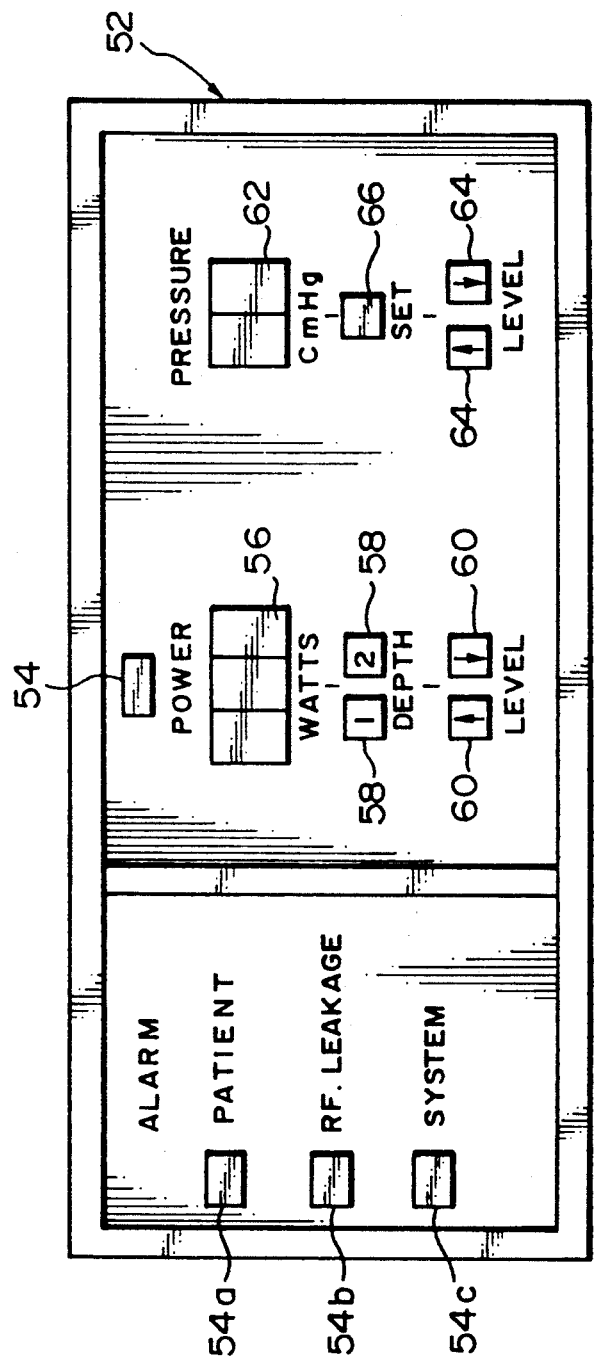
FIG. 5 is an explanatory view of the control panel in the first embodiment.

FIG. 5 shows the arrangement of the keys of the control panel 52. On the panel 52 are arranged a POWER lamp 54 indicating that the working power is generated, an output display 56 for displaying the set value of the working power, a mode selection key 58 for selecting the depth of the blood coagulation spot, an output value setting key 60 for increasing or reducing the value of the working power, a pressure display 62 for displaying the set value of the pressure of the liquid pump 28, a pressure setting key 64 for increasing or reducing the pressure of the liquid pump 28 and a liquid pump actuating key 66 for preliminarily supplying the electrolytic solution so as to enable the electrolytic solution to be immediately ejected when the liquid pump 28 is actuated. In addition to these keys, ALARM display lamps 54a, 54b and 54c are also provided.

In operating this apparatus, the handpiece 14 provided with the active electrode 16 and the counter electrode plate 20, etc. are first set, and the counter electrode plate 20 is connected to the living body in contact therewith. The liquid pump actuating key 66 on the control panel 52 is pressed to preliminarily supply the electrolytic solution as far as the liquid passage 26 (see FIG. 3) of the active electrode 16. In this state, the values of the working power and the pressure of the liquid pump 28 are set by the operations of the corresponding keys 60, 64 on the control panel 52.

In this embodiment, it is possible to select the depth of a blood coagulation spot by selecting the mode key [1] or [2] of the keys 58. If the mode [1] is selected, a blood coagulation spot having a comparatively small depth is formed on the surface of the tissue, while if the mode [2] is selected, a blood coagulation spot having a comparatively large depth is formed. To state this concretely, when the key [1] is pressed, the control unit 42 receives the signal from the control panel 52 and changes over the load characteristic switching circuit 46 to the high impedance side. This operation enables the value of the current flowing between the active electrode 16 and the living body which is connected to the counter electrode plate 20 to be reduced. When the current value is small, the diameter of the key [2] is pressed, the load characteristic switching circuit 46 is changed over to the low impedance side, and the value of the current flowing from the active electrode 16 becomes large. The diameter of the discharge column produced by the arc discharge becomes large and the permeability also increases, so that the blood coagulation proceeds to a deep portion of the living body.

When the above-described setting operation is finished and the operator turns on the switch 34 of the handpiece 14 or turns on the foot switch 51, the control unit 42 actuates each of the amplifier 44 and the pumps 28 and 38, respectively. By this operation, the electrolytic solution is atomized and ejected from the end portion of the handpiece 14. When the handpiece 14 is brought close to the bleeding portion of the living body, the arc discharge is produced through the route of ejection as a conduction path and can uniformly heat the bleeding portion in the range in which the atomized electrolytic solution is sprayed, thereby coagulating the blood.

That is, since the ejected electrolytic solution constitutes a conduction path having a comparatively low impedance, the arc discharge is produced without allowing the local presence of the atomized electrolytic solution.

In this embodiment, the high-frequency power can be adjusted by the key 60 on the control panel 52. This is because the control unit 42 controls the amplifier 44 so as to adjust the power in accordance with the operation of the key 60.

Second Embodiment

Figure 6:
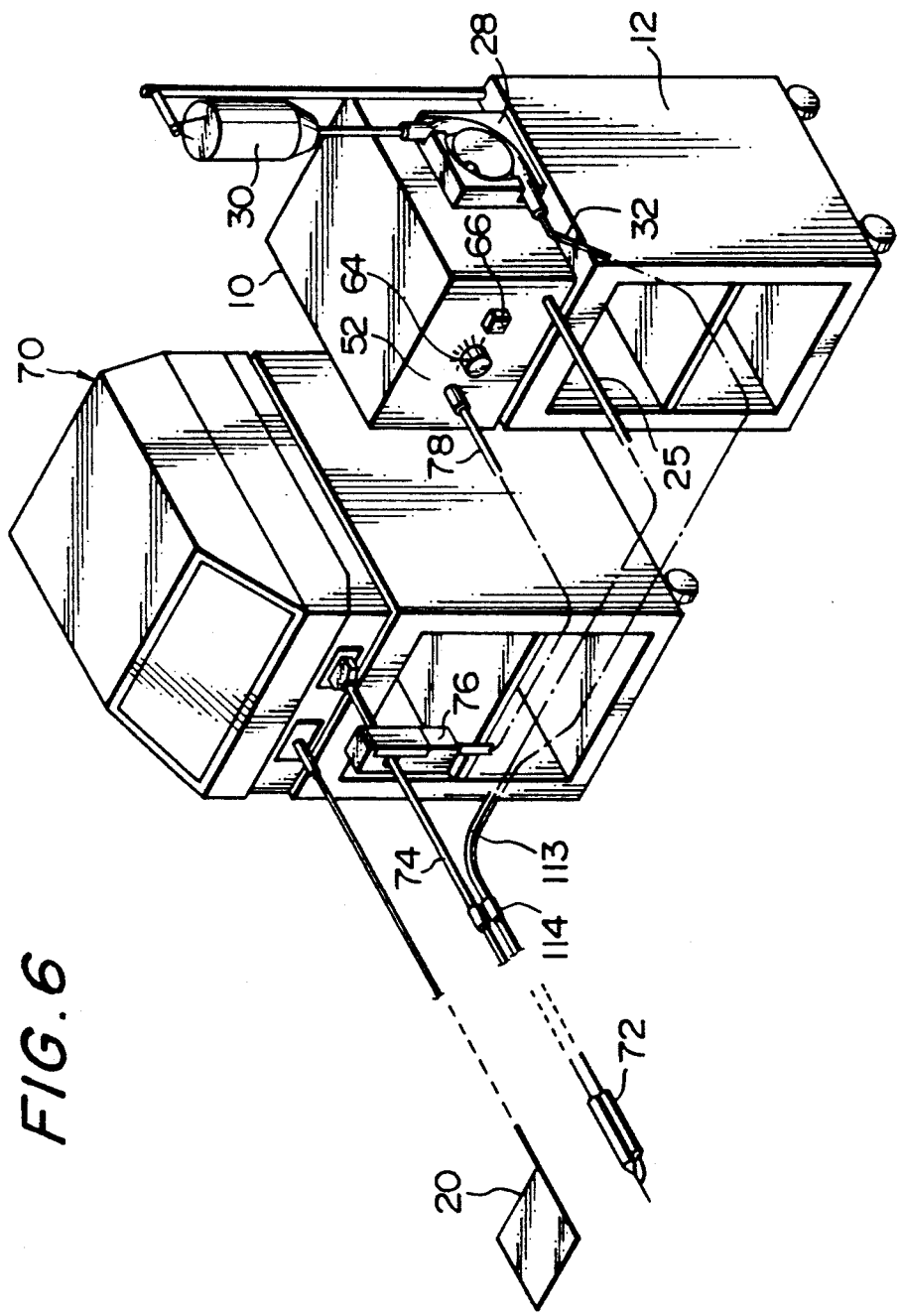
FIG. 6 is a schematic perspective view of the entire structure of a second embodiment of the present invention.

FIG. 6 is a perspective view of an external appearance of a second embodiment of a blood coagulating apparatus according to the present invention which is mounted on a conventional electrosurgical apparatus. The same reference numerals are provided for those elements which are the same as those shown in FIG. 1. A current sensor 76 is connected to an intermediate point of a connecting cable 74 of a handpiece 72 of an electrosurgical apparatus 70, and a signal supply line 78 of the current sensor 76 is connected to the main body 10 of the blood coagulating apparatus.

Figure 7:
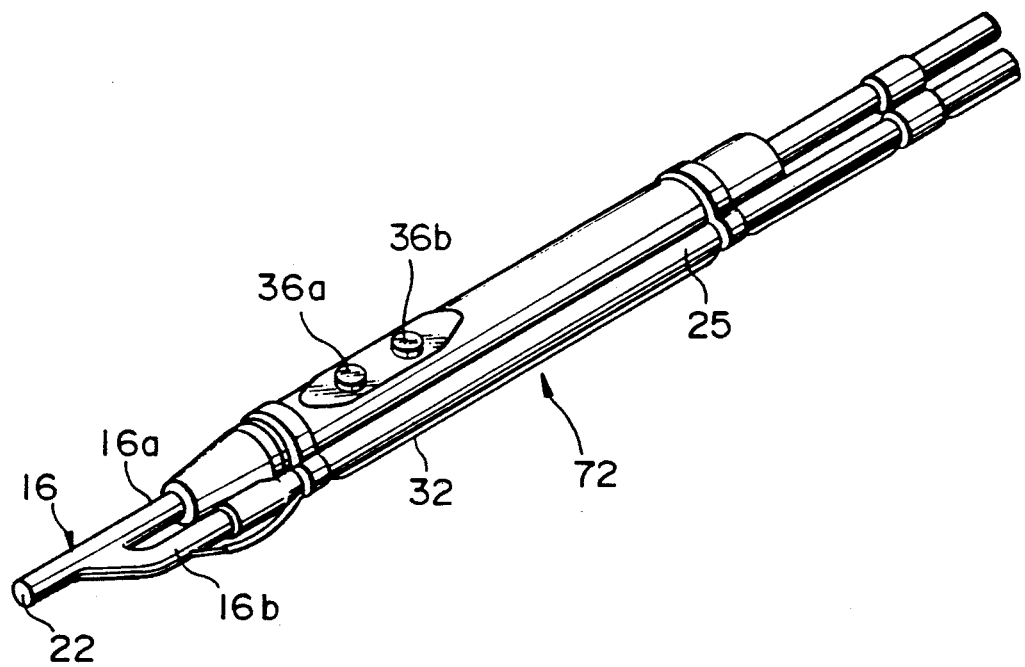
FIG. 7 is a perspective view of a handpiece used in the second embodiment shown in FIG. 6.
Figure 8:
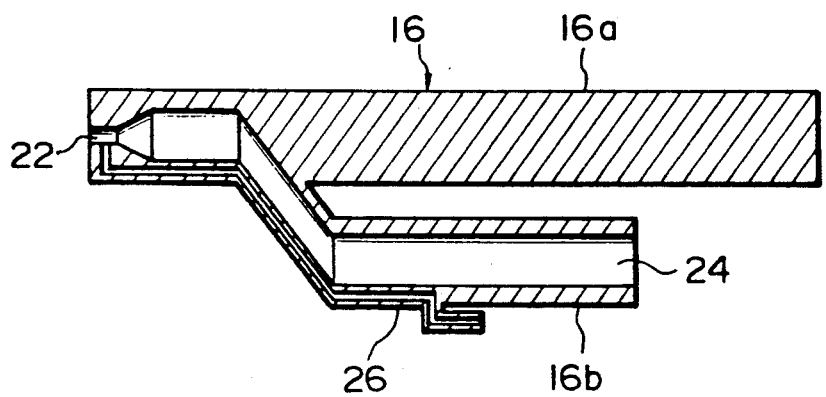
FIG. 8 is a schematic sectional view of the active electrode portion of the handpiece shown in FIG. 7.

FIG. 7 is a perspective view of the structure of the handpiece 72 in this embodiment. The ejection hole 22 is provided in the active electrode 16 at the end of the handpiece 72. The inner structure of the end portion of the active electrode 16 is shown in FIG. 8. As shown in FIG. 8, the active electrode 16 is branched halfway into a leg 16a on the power supply side to which the power is supplied from the main body of the electrosurgical apparatus 70 and a leg 16b on the liquid supply side to which the compressed air and the electrolytic solution are supplied from the main body 10 of the blood coagulating apparatus. The air passage 24 of the leg 16b is connected to the air tube 25 provided within the main body 10 of the blood coagulating apparatus, and the liquid passage 26 is connected to the liquid tube 32 of the liquid pump 28 provided on the main body 10.

In this way, in the case of mounting the blood coagulating apparatus of the present invention on a conventional electrosurgical apparatus, the forked handpiece 72 having a structure such as that shown in FIG. 8 is used.

Figure 9:
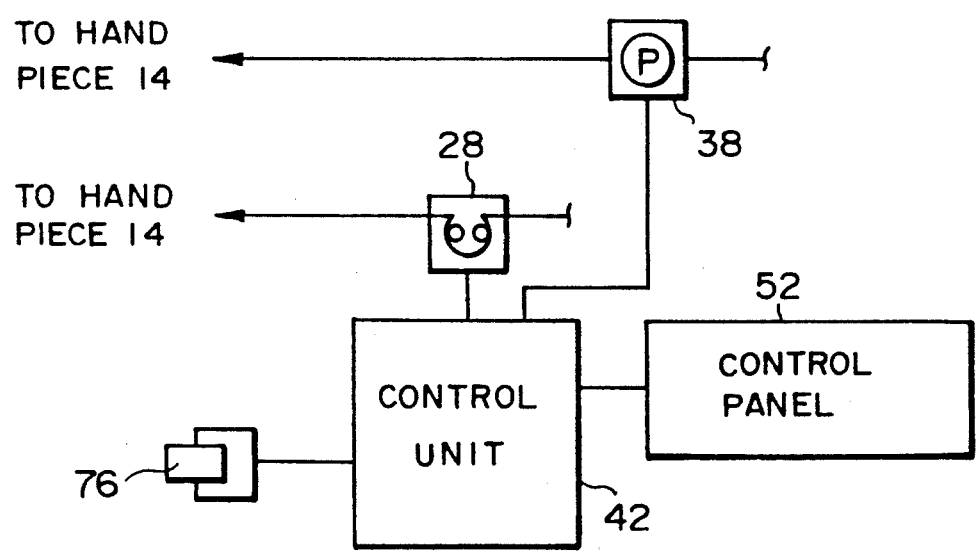
FIG. 9 is a circuit diagram of the main part of the second embodiment.

FIG. 9 shows the main part of the circuit of the second embodiment. The operation of this embodiment will be explained with reference to the circuit diagram.

This embodiment is characterized in that the current sensor 76 is connected to the control unit 42. The current sensor 76 detects the current flowing when the discharge is produced by the handpiece 72 of the electrosurgical apparatus.

The main body of the electrosurgical apparatus 70 is first prepared by an ordinary operation and the spray coagulation mode for coagulating the blood by the handpiece 72 of the electrosurgical apparatus is set (high voltage). The operator then operates the handpiece 72 so as to generate an output for spray coagulation, in other words, to produce the discharge between the active electrode 16 and the living body. The current flowing on the handpiece 72 when the first arc discharge is produced is detected by the current sensor 76 which is connected to the cable 74. The current sensor 76 which has detected the current transmits a current detection signal to the control unit 42. The control unit 42 supplies an actuation signal to the air pump 28 and a liquid pump 38 to actuate them. As a result, the atomized electrolytic solution is ejected from the ejection hole 22 at the end of the active electrode 16. The ejection of the electrolytic solution is continued by the operator during the discharging operation or it is so controlled as to be continued from the start of the ejection which is made by the first discharge till the switch for the spray coagulation is turned off by the operator.

In this way, the second embodiment functions as a blood coagulating apparatus according to the present invention when the handpiece 72 shown in FIGS. 7 and 8 and the current sensor 76 are mounted on a conventional electrosurgical apparatus.

As described above, according to a blood coagulating apparatus of the present invention, since the hemostatic operation is possible in the state in which the active electrode and the bleeding portion of the living body are not in contact with each other, and it is possible to form a uniform coagulation spot in a predetermined range by atomizing and ejecting the electrolytic solution and using the path of the ejected electrolytic solution as a conduction path, hemostatis of the living body utilizing the electric discharge is enabled with efficiency.

While there has been described what is at present considered to be a preferred embodiment of the invention, it will be understood that various modifications may be made thereto, and it is intended that the appended claims cover all such modifications as fall within the true spirit and scope of the invention.

What is claimed is:

1. A blood coagulating apparatus for stopping bleeding by heating the bleeding portion of the living body by discharge produced in the vicinity of said bleeding portion, said blood coagulating apparatus comprising:
    (a) a counter electrode plate which is capable of maintaining the state of being electrically connected to the living body;
    (b) an active electrode adapted to be introduced to the vicinity of said bleeding portion of the living body and including an electrolyte ejecting means for ejecting an atomized electrolyte toward said bleeding portion of the living body; and
    (c) a power source means for applying a high-frequency voltage between said counter electrode plate and said active electrode.

2. A blood coagulating apparatus according to claim 1, wherein said electrolyte ejecting means of said active electrode is composed of an ejector including an air passage for passing air therethrough at a high speed and a liquid passage for supplying said electrolyte to said air passage, said ejector atomizing said electrolyte while mixing air therewith and ejecting the atomized electrolyte toward said bleeding portion of the living body.

3. A blood coagulating apparatus according to claim 2, further comprising:
a current sensor means for detecting the current applied to said active electrode; and
an electrolyte supplying means for supplying said electrolyte on the basis of a signal output from said current sensor means.

4. A blood coagulating apparatus according to claim 3, further comprising a means for varying an intensity of the blood coagulating operation on the living body by varying an impedance of said high-frequency voltage which is applied between said active electrode and said counter electrode plate.

5. A blood coagulating apparatus according to claim 4, wherein the impedance of said high-frequency voltage which is applied between said active electrode and said counter electrode plate is sequentially varied by said coagulation intensity variation means.

6. A blood coagulating apparatus according to claim 5, wherein said electrolyte injecting means further includes an electrolyte preliminarily supplying means for preliminarily supplying said electrolyte to said liquid passage through which said electrolyte is supplied to said air passage for passing air therethrough at a high speed.

7. A blood coagulating apparatus according to claim 4, wherein said electrolyte injecting means further includes an electrolyte preliminarily supplying means for preliminarily supplying said electrolyte to said liquid passage through which said electrolyte is supplied to said air passage for passing air therethrough at a high speed.

8. A blood coagulating apparatus according to claim 3, wherein said electrolyte injecting means further includes an electrolyte preliminarily supplying means for preliminarily supplying said electrolyte to said liquid passage through which said electrolyte is supplied to said air passage for passing air therethrough at a high speed.

9. A blood coagulating apparatus according to claim 2, further comprising a means for varying an intensity of the blood coagulating operation on the living body by varying an impedance of said high-frequency voltage which is applied between said active electrode and said counter electrode plate.

10. A blood coagulating apparatus according to claim 9, wherein the impedance of said high-frequency voltage which is applied between said active electrode and said counter electrode plate is sequentially varied by said coagulation intensity variation means.

11. A blood coagulating apparatus according to claim 10, wherein said electrolyte injecting means further includes an electrolyte preliminarily supplying means for preliminarily supplying said electrolyte to said liquid passage through which said electrolyte is supplied to said air passage for passing air therethrough at a high speed.

12. A blood coagulating apparatus according to claim 9, wherein said electrolyte injecting means further includes an electrolyte preliminarily supplying means for preliminarily supplying said electrolyte to said liquid passage through which said electrolyte is supplied to said air passage for passing air therethrough at a high speed.

13. A blood coagulating apparatus according to claim 2, wherein said electrolyte injecting means further includes an electrolyte preliminarily supplying means for preliminarily supplying said electrolyte to said liquid passage through which said electrolyte is supplied to said air passage for passing air therethrough at a high speed.

14. A blood coagulating apparatus according to claim 1, further comprising:
a current sensor means for detecting the current applied to said active electrode; and
an electrolyte supplying means for supplying said electrolyte on the basis of a signal output from said current sensor means.

15. A blood coagulating apparatus according to claim 14, further comprising a means for varying an intensity of the blood coagulating operation on the living body by varying an impedance of said high-frequency voltage which is applied between said active electrode and said counter electrode plate.

16. A blood coagulating apparatus according to claim 15, wherein the impedance of said high-frequency voltage which is applied between said active electrode and said counter electrode plate is sequentially varied by said coagulation intensity variation means.

17. A blood coagulating apparatus according to claim 1, further comprising a means for varying an intensity of the blood coagulating operation on the living body by varying an impedance of said high-frequency voltage which is applied between said active electrode and said counter electrode plate.

18. A blood coagulating apparatus according to claim 17, wherein the impedance of said high-frequency voltage which is applied between said active electrode and said counter electrode plate is sequentially varied by said coagulation intensity variation means.

* * * * *